United States Patent
Bromberg et al.

(10) Patent No.: US 6,325,539 B1
(45) Date of Patent: Dec. 4, 2001

(54) CALIBRATION SIMPLIFICATION FOR A COMPUTED TOMOGRAPH SYSTEM

(75) Inventors: Neil B. Bromberg, Milwaukee; Tin-Su Pan, Brookfield, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/356,535

(22) Filed: Jul. 19, 1999

Related U.S. Application Data (60) Provisional application No. 60/114,477, filed on Dec. 31, 1998.

(51) Int. Cl.[7] ............................................. A61B 6/03
(52) U.S. Cl. ............................ 378/207; 378/4; 378/19
(58) Field of Search ................................. 378/207, 4, 19

(56) References Cited

U.S. PATENT DOCUMENTS

| | | | |
|---|---|---|---|
| 4,991,189 | * 2/1991 | Boomgaarden et al. | 378/19 |
| 5,612,985 | * 3/1997 | Toki et al. | 378/4 |
| 5,748,768 | * 5/1998 | Sivers et al. | 378/21 |
| 5,761,257 | * 6/1998 | Toth et al. | 378/4 |
| 5,764,720 | * 6/1998 | Besson | 378/4 |
| 5,864,598 | * 1/1999 | Hsieh et al. | 378/4 |
| 5,907,593 | * 5/1999 | Hsieh et al. | 378/4 |
| 6,061,419 | * 5/2000 | Hsieh et al. | 378/4 |
| 6,075,835 | * 6/2000 | Acharya et al. | 378/4 |
| 6,091,797 | * 7/2000 | Xie et al. | 378/62 |
| 6,118,840 | * 9/2000 | Toth et al. | 378/4 |
| 6,134,292 | * 10/2000 | Hsieh | 378/4 |
| 6,137,857 | * 10/2000 | Hoffman et al. | 378/4 |

* cited by examiner

Primary Examiner—Drew Dunn
(74) Attorney, Agent, or Firm—Armstrong Teasdale LLP; Christian G. Cabou (57) ABSTRACT

Methods and apparatus for calibration simplification in a computed tomography (CT) system are described. In one embodiment, the CT system utilizes calibration values from a first scan type, or mode of operation, to determine calibration values for at least a second scan type. As a result, the time required to perform calibration of the CT system is reduced.

25 Claims, 7 Drawing Sheets

CALIBRATION SIMPLIFICATION FOR A COMPUTED TOMOGRAPH SYSTEM

CROSS REFERENCE TO RELATED APPLICATION

This application claims the benefit of U.S. Provisional Application No. 60/114,477, filed Dec. 31, 1998.

BACKGROUND OF THE INVENTION

This invention relates generally to computed tomograph (CT) imaging and, more particularly, to a calibration of a CT system.

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a post patient collimator for collimating scattered x-ray beams received at the detector. A scintillator is located adjacent the post patient collimator, and photodiodes are positioned adjacent the scintillator.

Uniformity between individual detector elements is important for securing good image quality of CT images. Otherwise, anomalies may occur in the collected data. A consequence of data anomalies are image distortions, commonly referred to as artifacts. Detector uniformity may be impacted by many factors including radiation damage and sensitivity of the scintillator materials. To correct for this uniformity, periodic calibrations of the detector are required.

A common method for calibration employs devices known as a phantoms. Different size phantoms, providing known attenuation paths for x-ray beams passing therethrough, are utilized to generate calibration data for different size objects. Using any non-uniformity demonstrated during the calibration, an error value is generated for the specific size object. The generated error value is then used to correct the measured values of the detector so that detector response is uniform for subsequent use when imaging a patient.

The calibration method, described above, has the major drawback of requiring separate calibrations for different modes of operation, or scan types, of the imaging system. These scans include different size objects and different types of filtration of the x-ray beam, using a filtration device. Such a filtration device, in one known system, is a bow-tie filter having a head portion and a body portion. As a consequence, a separate calibration must be performed for each scan type. Therefore, the calibration of the imaging system is very time consuming and is likely to cause inconvenience to the CT system operator.

Accordingly, it would be desirable to provide a CT system that reduces the number of calibration scans which must be performed. It is also desirable to provide a method for utilizing calibration data from a first scan type to determine the error value for other scan types.

BRIEF SUMMARY OF THE INVENTION

These and other objects may be attained by a CT system which, in one embodiment, utilizes calibration values from a first type of calibration scan to determine the calibration values for at least a second type of calibration scan of the system. The CT system, in one embodiment, includes an x-ray source, a detector array, and a filtration device. The CT system detector, in one embodiment, includes a multislice detector.

In one embodiment, prior to scanning a patient, first calibration scan attenuation data is collected by radiating x-ray beams through a phantom. The collected attenuation data is then compared to ideal attenuation data for the phantom and a difference value is generated for each detector element. The difference values are then used to determine the first type of calibration scan values. Values from the first type of calibration scan are then used to determine calibration values for at least the second type of scan. After selecting a scan type, the patient scan is completed. The attenuation data collected during the patient scan is then adjusted by the selected calibration scan values.

By using the above described CT system the number of calibration scans is reduced. In addition, such calibration improves CT system efficiency and improves system availability.

DETAILED DESCRIPTION OF THE INVENTION

Set forth below is a description of an exemplary multislice CT system in accordance with one embodiment of the present invention. Although one embodiment of the system is described in detail below, it should be understood that many alternative embodiments of the inventions are possible. For example, although one particular detector and one particular pre-patient collimator are described, other detectors or collimators could be used in connection with the system, and the present invention is not limited to practice with any one particular type of detector. Specifically, the detector described below includes a plurality of modules and each module includes a plurality of detector elements, or cells. Rather than the specific detector described below, a detector which has non-segmented cells along the z-axis, and/or a detector which has multiple modules with multiple elements along the x-axis and/or z-axis joined together in either direction to acquire multislice scan data simultaneously, can be utilized. Generally, the system is operable in a multislice mode to collect 1 or more slices of data. Axial and helical scans can be performed with the system, and cross section images of a scanned object can be processed, reconstructed, displayed and/or archived.

Figure 1:
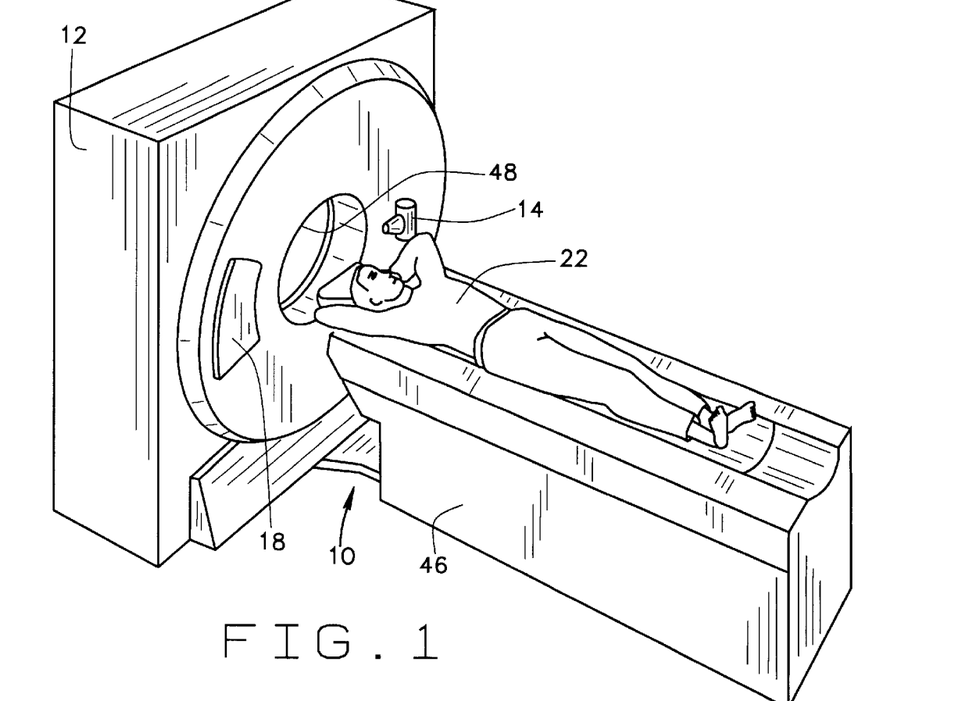
FIG. 1 is a pictorial view of a CT imaging system.
Figure 2:
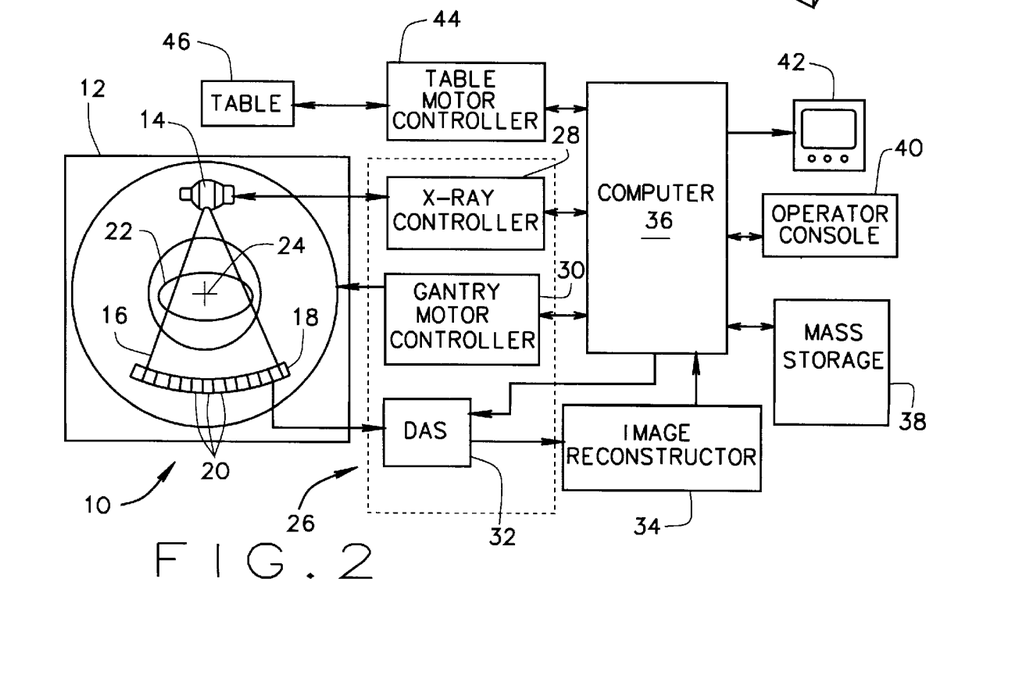
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector modules 20 which together sense the projected x-rays that pass through a medical patient 22. Each detector module 20 produces electrical signals that represent the intensity of impinging x-ray beams and hence the attenuation of the beams as they pass through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples data from detector modules 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 also operates a table motor controller 44 which controls a motorized table 46 to position patient 22 in gantry 12. Particularly, table 46 moves portions of patient 22 through a gantry opening 48.

Figure 3:
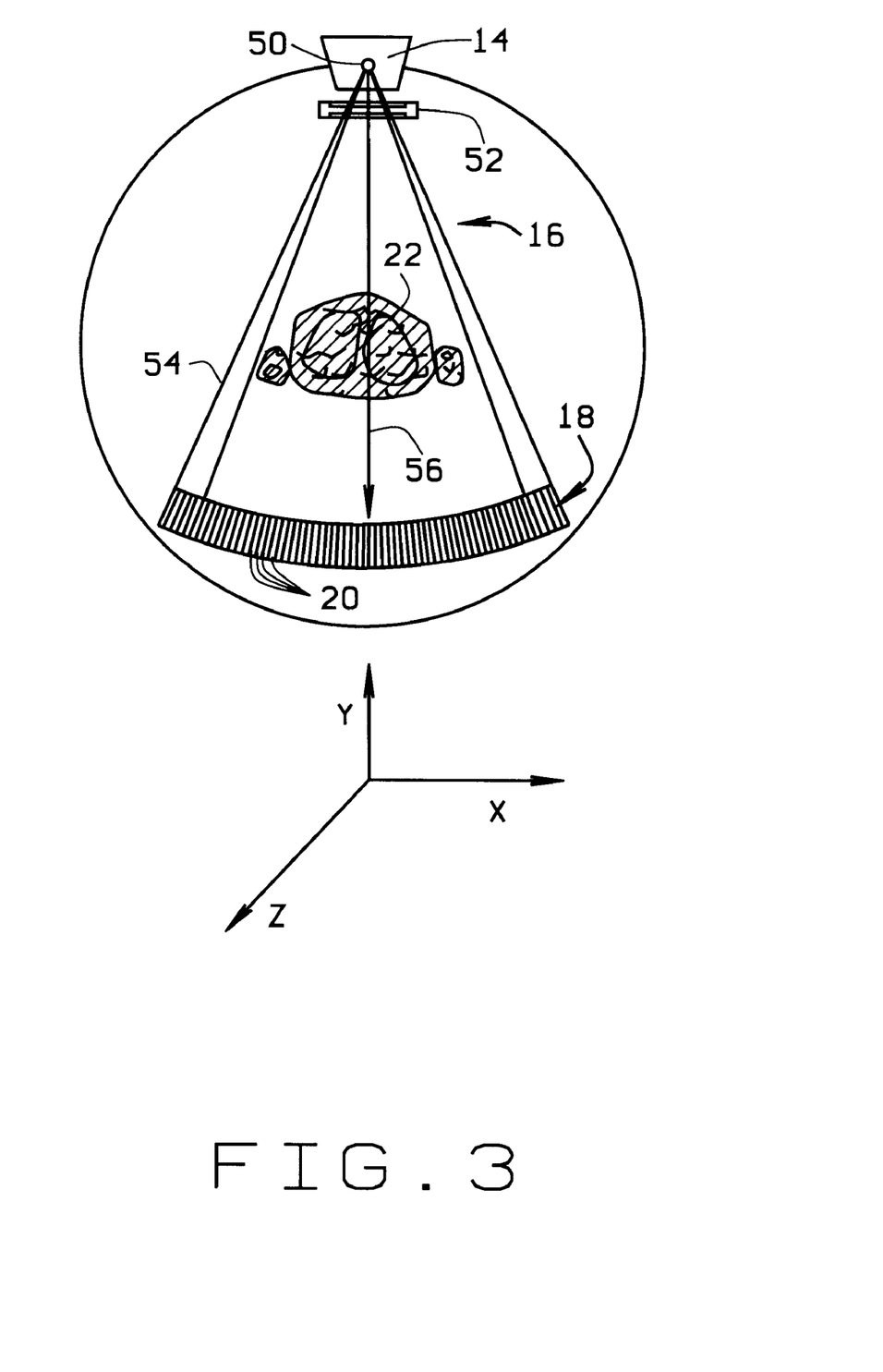
FIG. 3 is a schematic view of the CT imaging system with a collimator.

Referring to FIG. 3, and with respect to operation of x-ray source 14, x-ray beam 16 emanates from a focal spot 50 of source 14. X-ray beam 16 is collimated by a pre-patient collimator 52, and a collimated beam 54 is projected toward detector array 18 along a fan beam axis 56 centered within beam 16. In one embodiment, collimator 52 includes a bow-tie filter (not shown) having a head portion and a body portion (not shown). The different portions of the filter define the amount of x-ray beam 16 that is allowed to pass through the bow-tie filter. For example, if the head of patient 22 is to be scanned, the position of the bow-tie filter is adjusted so that the filter reduces x-ray beam 16 to a head mode type exposure.

Figures 4, 5:
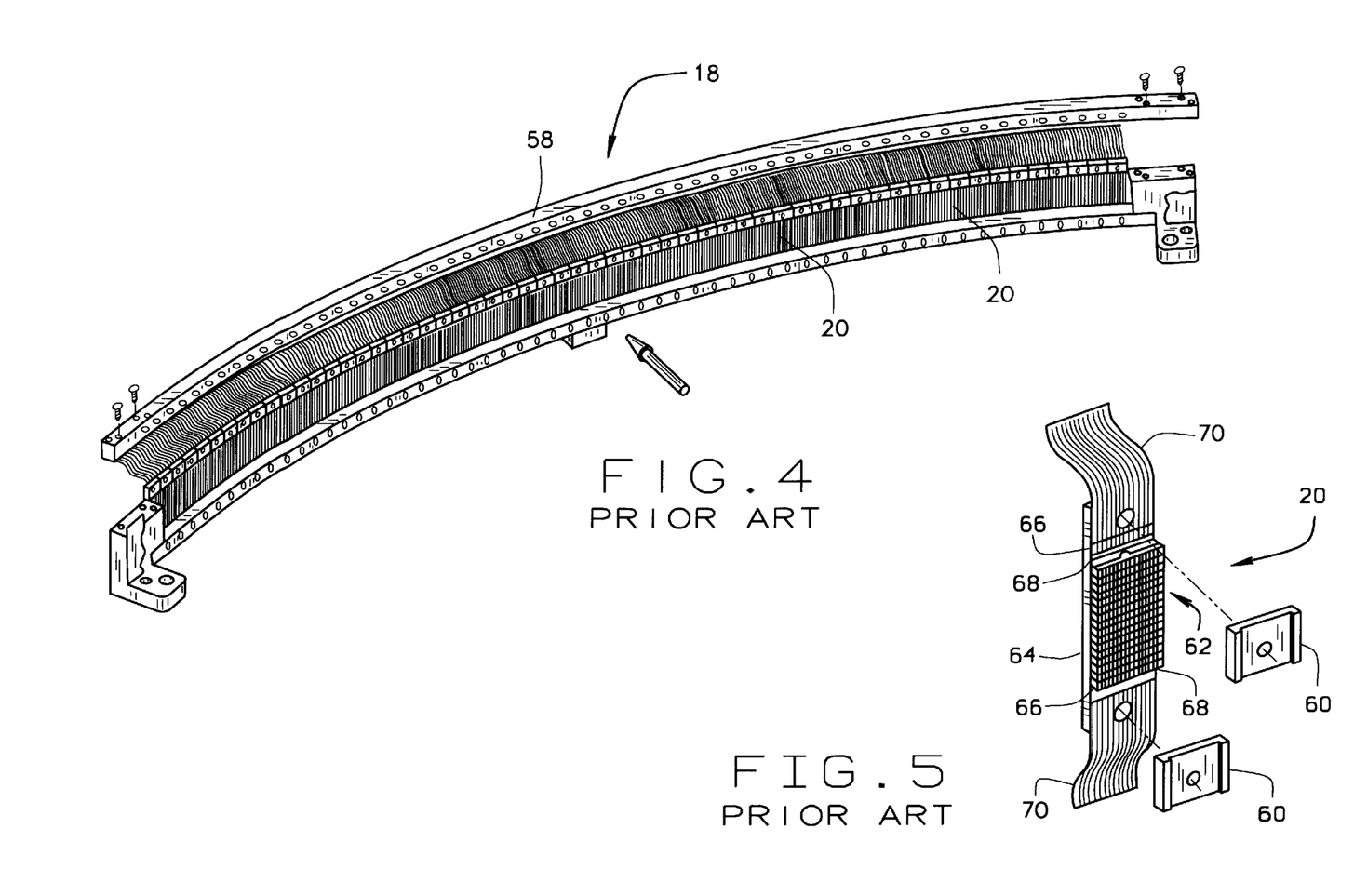
FIG. 4 is a perspective view of a prior art CT system detector array utilized in one embodiment of the present invention.
FIG. 5 is a perspective view of a prior art detector module utilized in the CT system detector array of FIG. 4.

As shown in FIGS. 4 and 5, detector array 18 includes a plurality of detector modules 20. Each detector module 20 is secured to a detector housing 58 by plates 60. Each module 20 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 20 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of photodiode array 52 are electrically connected to DAS 32, resulting in 16 separate, simultaneous slices of data being sent to DAS 32. Of course, many other slice combinations are possible.

In one specific embodiment, detector 18 includes fifty-seven detector modules 20. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 6:
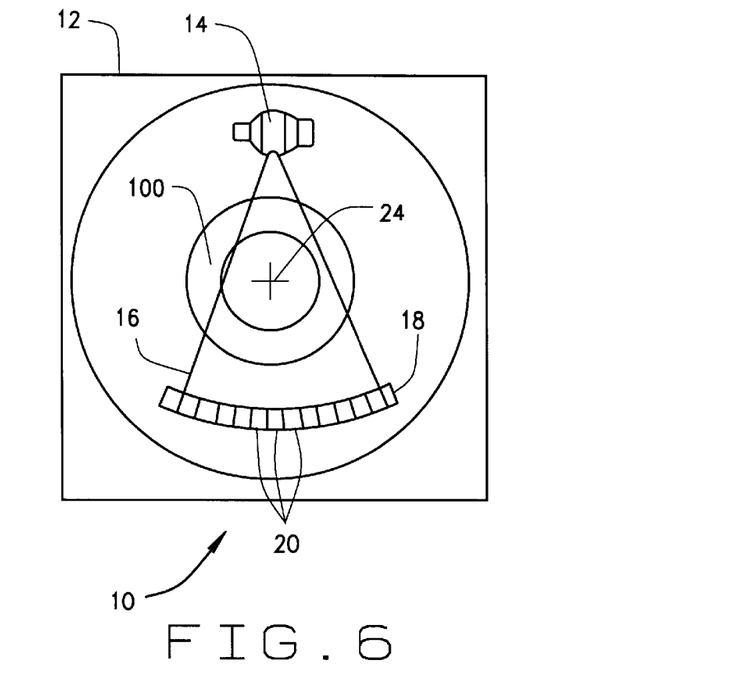
FIG. 6 is a representation of calibration of a CT imaging system utilizing a phantom in one embodiment of the present invention.

In operation, prior to scanning patient 22, system 10 is calibrated. In order to reduce the number of scans required to be performed, calibration values from a first type of calibration scan are utilized to determine values for at least a second type of calibration scan. In one embodiment, and referring to FIG. 7, system 10 is calibrated by selecting a first type of calibration scan 104 and scanning 106 a first phantom 100 placed within gantry 12. More specifically, and as shown in FIG. 6, phantom 100 is positioned so that as x-ray beams 16 are emitted from x-ray source 14, beams 16 pass through phantom 100. In one embodiment, phantom 100 is disk-shaped, made of polytetrafluoroethylene, and has a diameter of approximately 35 cm. Of course other sizes and shapes of phantom 100 may be utilized.

Figure 7:
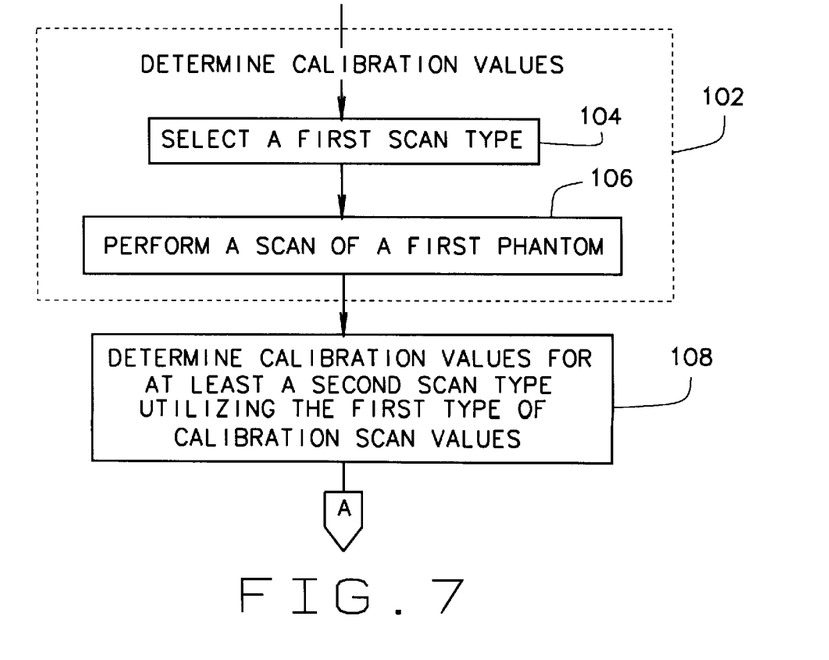
FIG. 7 is a flow chart representative of one embodiment of the present invention.
Figure 8:
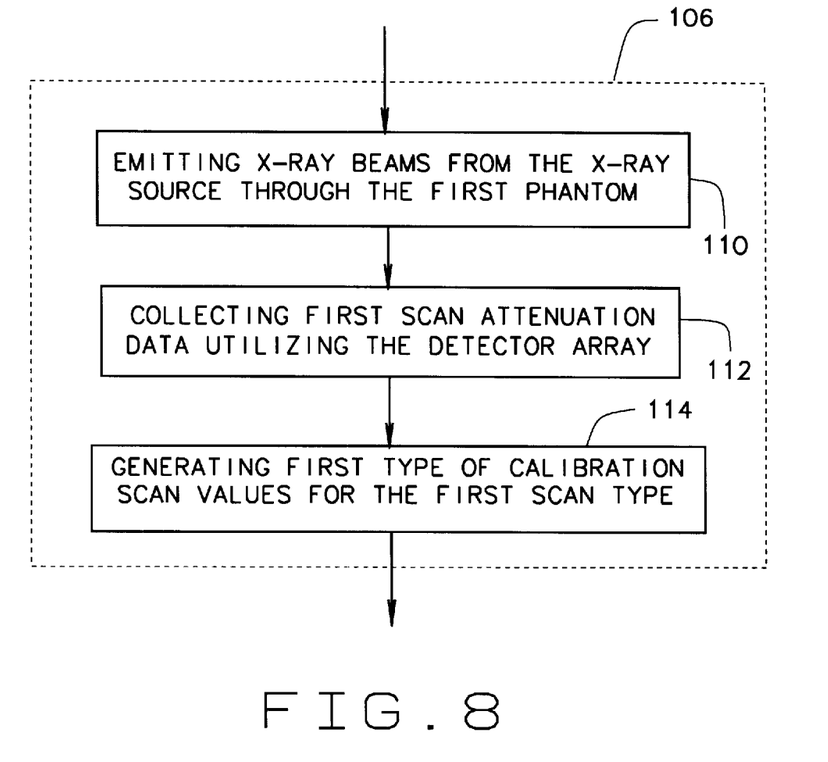
FIG. 8 is a flow chart representing steps comprising performing a scan of a first phantom in one embodiment of the present invention.

Referring to FIGS. 6 and 7, after positioning phantom 100, a scan of phantom 100 is performed to determine 102 the calibration values for the first scan type of system 10. More specifically, and referring to FIG. 8, a calibration value is determined for each detector element, or cell, by emitting 110 x-ray beams 16 from x-ray source 14 through phantom 100. First scan type attenuation data is then collected 112 utilizing detector array 18. Particularly, an attenuation signal, representative of the intensity of beam 16, is generated for each detector element (not shown). The attenuation signals, or data, are supplied to DAS 32. Using various known techniques, image data of phantom 100 then is generated and compared to ideal image data of phantom 100, for example using computer 36. By determining a difference between the ideal image data and the attenuation data, a first type of calibration scan value is determined 114 for each element of detector array 18. Particularly, the determined first type of calibration scan values represent the adjustment, or correction, of the signals collected by detector array 18 of system 10 operating in a first type of scan.

Again referring to FIG. 7, utilizing the calibration values from the first type of calibration scan, calibration values for at least a second scan type are determined 108. More place, specifically, in one embodiment and referring to FIGS. 7, 9, and 10 the first type of calibration scan values are utilized directly for at least the second type of calibration scan 108. For example, where the scan types of system 10 include at least two of a large body bow-tie calibration scan, a medium body bow-tie calibration scan, a medium head bow-tie calibration scan, a small head bow-tie calibration scan, an air calibration scan, a body bow-tie calibration scan, and a head bow-tie calibration scan, and the first scan type is the medium body bow-tie calibration scan type 116, 118, calibration values for the large calibration body bow-tie and small head bow-tie scan types are determined utilizing the first type of calibration scan values.

Figure 9:
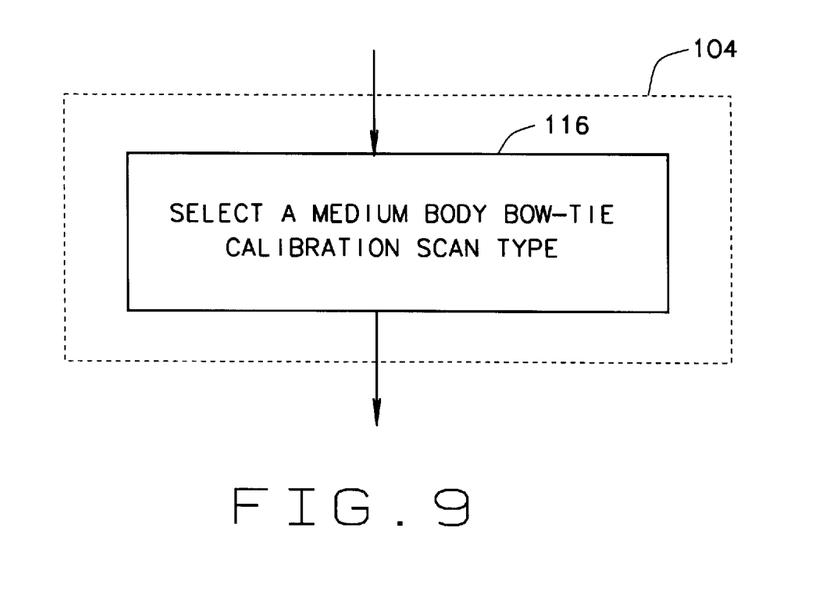
FIG. 9 is a flow chart representing a step comprising selection of a first scan type in one embodiment of the present invention.
Figure 10:
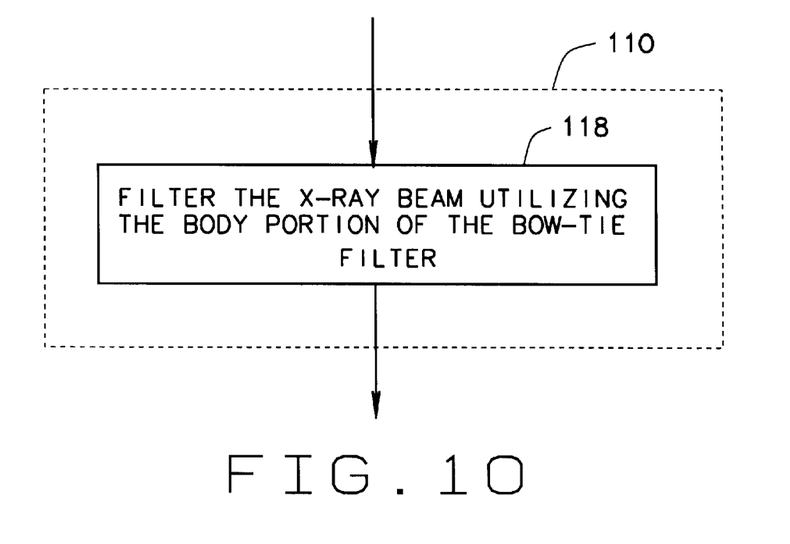
FIG. 10 is a flow chart representing a step comprising emitting x-ray beams from the x-ray source through a first phantom in one embodiment of the present invention.

More specifically, the calibration value for each respective detector element for the medium body bow-tie calibration scan is equal to the respective calibration value for each detector element of the large calibration body bow-tie and small head bow-tie scans. As a result, the calibration values may be used to correct attenuation data collected from system 10 operating in a first scan type, a second scan type, or a third scan type. Therefore, the amount of time required to calibrate system 10 is reduced and availability of system 10 is improved.

Figure 11:
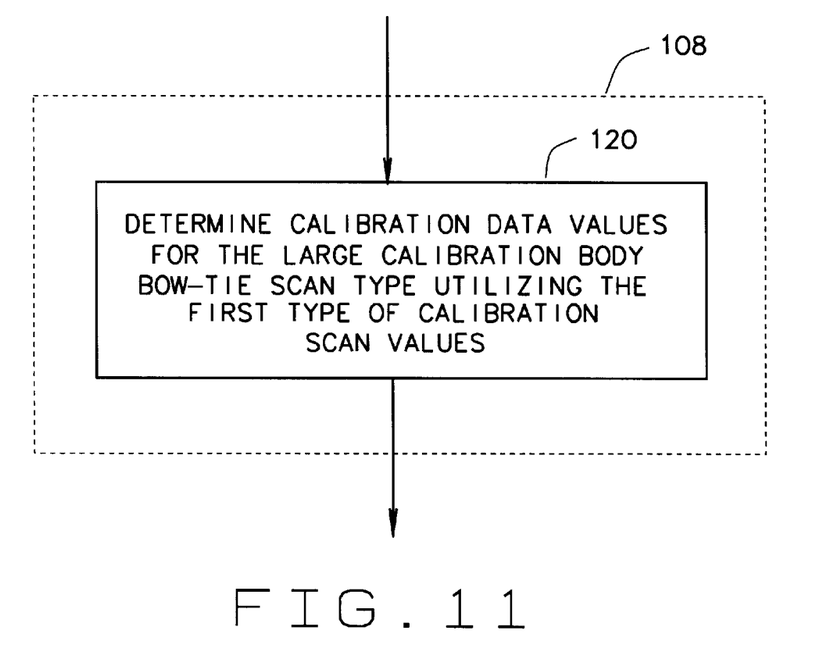
FIG. 11 is a flow chart representing a step comprising determining calibration values for at least a second scan type utilizing the first scan type of calibration scan values in one embodiment of the present invention.

For example, the availability of system 10 may be significantly improved by utilizing the first type of calibration scan values for the second and third scan types. More specifically, if calibration values are measured for four voltage levels, two focal spots of source 14, and four apertures of collimator 52 for the air scan; body bow-tie; head bow-tie; large body bow-tie; medium body bow-tie; medium head bow-tie; and small head bow-tie scan types, 224 scans must be performed. Referring to FIG. 11, by utilizing the calibration data from the medium body bow-tie to determine 120 the large body bow-tie and small head bow-tie scan types, 32 scans, i.e. over 14% of the tests, are eliminated. Therefore the time required to perform periodic calibration is reduced. In other embodiments, various known interpolation techniques may be utilized to determine at least the second type of calibration scan values using the first type of calibration scan values.

Figure 12:
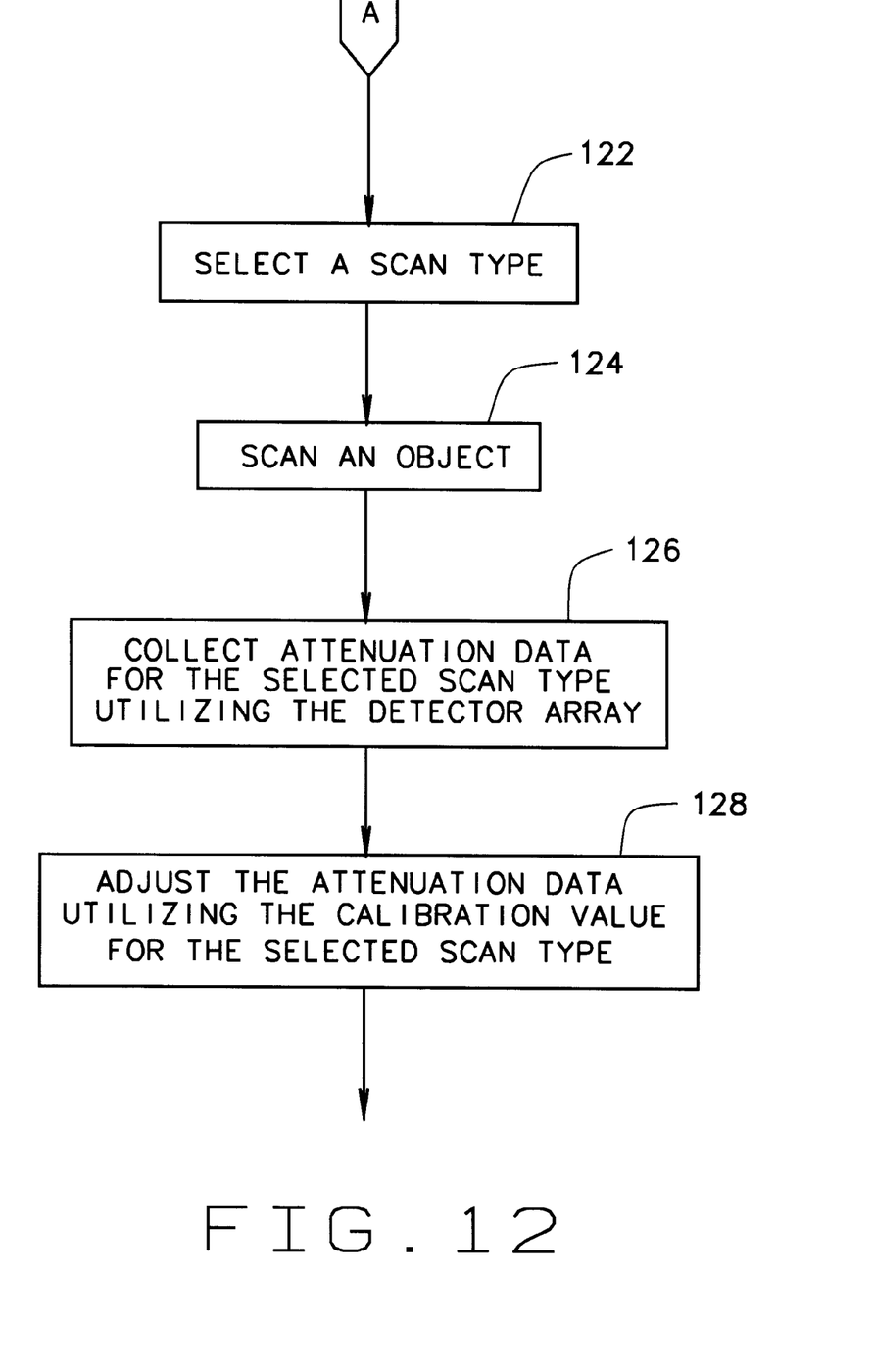
FIG. 12 is a flow chart representing additional steps performed after the steps shown in FIG. 7 in one embodiment of the present invention.

Referring to FIG. 12, after determining the calibration values for each scan type, a scan of patient 22 is completed 124 using the selected scan type 122, i.e., as determined by an operator. The attenuation data collected 126 using detector array 18 is then adjusted 128, or corrected, using the selected scan type calibration values. For example, attenuation data collected from the scan of patient 22 using the second scan type of system 10, is corrected by the generated second type of calibration scan values. More specifically, the attenuation data for each respective detector element is adjusted 128 by the respective calibration value of each element for the second scan type. As a result, the image generated from the adjusted data accurately reflects the scanned patient 22.

The above described CT system reduces the number of scans required to calibrate the system. In addition, such calibration improves CT system efficiency and improves system availability.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for calibration of a computed tomography (CT) system, the CT system including an x-ray source and a detector array, and wherein the system operable in at least two scan types, said method comprising:

determining calibration values for a first scan type; and determining calibration values for at least a second scan type utilizing the first type of calibration scan values.

2. A method in accordance with claim 1 wherein the scan types include at least two of a large body bow-tie calibration scan, a medium body bow-tie calibration scan, a medium head bow-tie calibration scan, a small head bow-tie calibration scan, an air calibration scan, a body bow-tie calibration scan, and a head bow-tie calibration scan.

3. A method for calibration of a computed tomography (CT) system, the CT system including an x-ray source and a detector array, and wherein the system operable in at least two scan types, said method comprising:

determining calibration values for a first scan type; and determining calibration values for at least a second scan type utilizing the first type of calibration scan values;

wherein the scan types include at least two of a large body bow-tie calibration scan, a medium body bow-tie calibration scan, a medium head bow-tie calibration scan, a small head bow-tie calibration scan, an air calibration scan, a body bow-tie calibration scan, and a head bow-tie calibration scan; and wherein determining calibration values for a first scan type comprises:

selecting a first scan type; and performing a scan of a first phantom.

4. A method in accordance with claim 3 wherein selecting a first scan type comprises selecting the medium body bow-tie calibration scan type.

5. A method in accordance with claim 4 wherein performing a scan of a first phantom comprises:

emitting x-ray beams from the x-ray source through the first phantom;

collecting first scan attenuation data utilizing the detector array; and generating fist type of calibration scan values for the first scan type.

6. A method in accordance with claim 5 wherein the CT system includes a bow-tie filter having a body portion and a head portion wherein emitting x-ray beams from the x-ray source through the first phantom comprises filtering the x-ray beams utilizing the body portion of the bow-tie filter.

7. A method in accordance with claim 6 wherein determining calibration values for at least a second scan type utilizing the first type of calibration scan values comprises determining calibration values for the large calibration body bow-tie scan type utilizing the first type of calibration scan values.

8. A method in accordance with claim 7 further comprising determining calibration values for the small head bow-tie scan type utilizing the first type of calibration scan values.

9. A method in accordance with claim 3 wherein the first phantom is a disk-shaped phantom made of polytetrafluorethylene.

10. A method in accordance with claim 3 wherein a diameter of the first phantom is 35 cm.

11. A method for calibration of a computed tomography (CT) system, the CT imaging system including an x-ray source and a detector array, and wherein the system operable in at least two scan types, said method comprising:

determining calibration values for a first scan type;

determining calibration values for at least a second scan type utilizing the first type of calibration scan values;

selecting a scan type;

scanning an object;

collecting attenuation data for the selected scan type utilizing the detector array; and adjusting the attenuation data utilizing the calibration value for the selected scan type.

12. A computed tomography (CT) system for generating an image of an object, said system comprising an x-ray source and a detector array and configured to operate in at least two scan types and:

determine calibration values for a first scan type; and determine calibration values for at least a second scan type utilizing said first type of calibration scan values.

13. A system in accordance with claim 12 wherein said scan types comprise at least two of a large body bow-tie calibration type, a medium body bow-tie calibration type, a medium head bow-tie calibration type, a small head bow-tie calibration scan, an air calibration scan, a body bow-tie calibration scan, and a head bow-tie calibration scan.

14. A computed tomography (CT) system for generating an image of an object, said system comprising an x-ray source and a detector array and configured to operate in at least two scan types and:

determine calibration values for a first scan type; and determine calibration values for at least a second scan type utilizing said first type of calibration scan values;

wherein said scan types comprise at least two of a large body bow-tie calibration type, a medium body bow-tie calibration type, a medium head bow-tie calibration type, a small head bow-tie calibration scan, an air calibration scan, a body bow-tie calibration scan, and a head bow-tie calibration scan; and wherein to determine calibration values for a first scan type, said system configured to:

select a first scan type; and perform a scan of a first phantom.

15. A system in accordance with claim 14 wherein to select a first scan type, said system configured to select the medium body bow-tie calibration scan type.

16. A system in accordance with claim 15 wherein to perform a scan of a first phantom, said system configured to:

emit x-ray beams from said x-ray source through said first phantom;

collect first scan attenuation data utilizing said detector array; and generate first type of calibration scan values for said first scan type.

17. A system in accordance with claim 16 further comprising a bow-tie filter having a body portion and a head portion, wherein to emit x-ray beams from said x-ray source through said first phantom, said system configured to filter said x-ray beams utilizing said body portion of said bow-tie filter.

18. A system in accordance with claim 17 wherein to determine calibration values for at least said second scan type utilizing said first type of calibration scan values, said system configured to determine calibration values for said large calibration body bow-tie scan type utilizing said first type of calibration scan values.

19. A system in accordance with claim 18 further configured to determine calibration values for said small head bow-tie scan type utilizing said first type of calibration scan values.

20. A system in accordance with claim 12 wherein said detector array is a multislice detector array.

21. A computed tomography (CT) system for generating an image of an object, said system comprising an x-ray source and a detector array and configured to operate in at least two scan types and:

determine calibration values for a first scan type; and determine calibration values for at least a second scan type utilizing said first type of calibration scan values;

select a scan type;

scan an object;

collect attenuation data for said selected scan type utilizing said detector array; and adjust said attenuation data utilizing said calibration value for said selected scan type.

22. A method for calibration of a computed tomography (CT) system, the CT system including an x-ray source and a detector array, and wherein the system operable in at least two scan types, said method comprising:

determining calibration values for a first scan type; and determining calibration values for at least a second scan type utilizing the first type of calibration scan values, wherein determining calibration values for a first scan type comprises:

selecting a first scan type; and performing a scan of a first phantom.

23. A method in accordance with claim 22 wherein performing a scan of a first phantom comprises:

emitting x-ray beams from the x-ray source through the first phantom;

collecting first scan attenuation data utilizing the detector array; and generating first type of calibration scan values for the first scan type.

24. A method in accordance with claim 23 wherein the CT system includes a bow-tie filter having a body portion and a head portion wherein emitting x-ray beams from the x-ray source through the first phantom comprises the step of filtering the x-ray beams utilizing the body portion of the bow-tie filter.

25. A computed tomography (CT) system for generating an image of an object, said system comprising an x-ray source and a detector array and configured to operate in at least two scan types and:

determine calibration values for a first scan type; and determine calibration values for at least a second scan type by interpolation, utilizing said first type of calibration scan values; and wherein to determine calibration values for a first scan type, said system configured to:

select a first scan type; and perform a scan of a first phantom.

* * * * *